US00PP09644P

United States Patent [19]

Pieper

[11] Patent Number: Plant 9,644

[45] Date of Patent: Sep. 17, 1996

[54] *AECHMEA FASCINI* VARIEGATED FRIEDERIKE'

[76] Inventor: Wilhelm K. H. Pieper, Dehmke, auf der Horst 2, 3258 Aerzen 9, Germany

[21] Appl. No.: 393,226

[22] Filed: Feb. 23, 1995

[51] Int. Cl.[6] ..... A01H 5/00

[52] U.S. Cl. ..... Plt./88.8

[58] Field of Search ..... Plt./88.8

[56] References Cited

U.S. PATENT DOCUMENTS

P.P. 5,872 2/1987 Pieper ..... Plt./88.3

P.P. 7,832 3/1992 DeLeon ..... Plt./88.8

*Primary Examiner*—James R. Feyrer

*Attorney, Agent, or Firm*—Howell & Haferkamp, L.C.

[57] ABSTRACT

A new variety of *Aechmea fascini* is disclosed which is characterized by variegated leaves (creamy white leaf margins) and the absence of spines along the margins of the leaves.

4 Drawing Sheets

DESCRIPTION

The present invention relates to a new and distinct variety of *Aechmea fascini* Friederike.

This new cultivation was developed by me in my laboratory at Aerzen, Federal Republic of Germany. Repeated asexual reproduction of the plants by offsets has shown that the unique feature of this new variety of *Aechmea fascini* Friederike (designated *Aechmea fascini* "Variegated Friederike") may be reproduced true to type in subsequent propagations.

The new cultivation is related to an earlier hybridization resulting from a cross of "*Ae. chantinii* ♀" with "*Ae. fasciata*" in Assendelft, Netherland, i.e., a seeding resulting from species hybridization. The resulting hybridization, however, turned out to be sterile, and was thus propagated via cell division by me during the years 1974 and 1975 and put on the market under the name "*Aechmea fascinii.*" No histological examinations as to aberrations of ploidy or as to mechanical defects of the blossoming organs were performed, as this is not common in a commercially run market gardening.

During commercial propagation, the "*Ae. fascini*" turned out to be genetically instable, and spontaneous mutations occurred repeatedly. As the reason therefor could not be found, "*Ae. fascinii*" must be regarded as a somaclonal mutation. There was a systematical search for a suitable type. What was found was "*Ae. friederike,*" another related plant. An application for "*Acehmea friederike*" was filed with the U.S. Patent Office on Nov. 6, 1984 and granted as U.S. Plant Pat. No. 5,872 on Feb. 3, 1987.

The clone "*Ae. friederike,*" however, also suffered from occasional mutations. The subject plant of this patent application, "*Ae. Variegated friederike,*" was discovered during the in vitro propagation of "*Ae. friederike,*" and given the name "Felicitas." There was no attempt of a somatic hybridization (nuclear fusion); rather, it is suspected that the new plant is a somaclonal variation, a mutation that has lost the chlorophyll in part of its cells either due to loss or duplication of chromosomes or due to alterations of genes—i.e., it is a pure chimera.

This new variety of plant may be compared with *Aechmea fascini* and with *Aechmea fascini* Friederike, the spineless variety of *Aechmea fascini* with the most striking comparision being that the new variety has variegated leaves with whitish cream-yellow and smooth margins while the leaves of *Aechmea fascini* Friederike are green and spineless and the leaves of *Aechmea fascini* are green with spines of approximately 4 mm in length and spaced about 10 mm apart. The absence of the spines is highly advantageous as it greatly facilitaes handling of the plant and the creamy leaf margins increase the ornamental value of the plant. The new variety otherwise retains the basic characteristics of the *Aechmea fascini* and of the *Aechmea fascini* Friederike; in particular, the color and shape of the blossom are the same. The plant is sterile and can be propagated only vegetatively by offsets.

Unlike "*Ae. friederike,*" it cannot be propagated any more through in vitro cultivation, because what is achieved thereby are either green plants ("*Ae. friederike*") or white plants lacking chlorophyll that can be bred in vitro up to a certain size, but which immediately die off in vivo due to lack of chlorophyll. It can be propagated only vegetatively, i.e., by lateral development (so-called "child"). As a plant has up to 14 vegetative points (lateral meristems), applicant has vegetatively propagated the plant and found that the average propagation rate is about 10 pieces per plant.

The accompanying drawings clearly depict the new variety and provide a comparison with *Aechmea fascini* Friederike, wherein.

Figure 1:
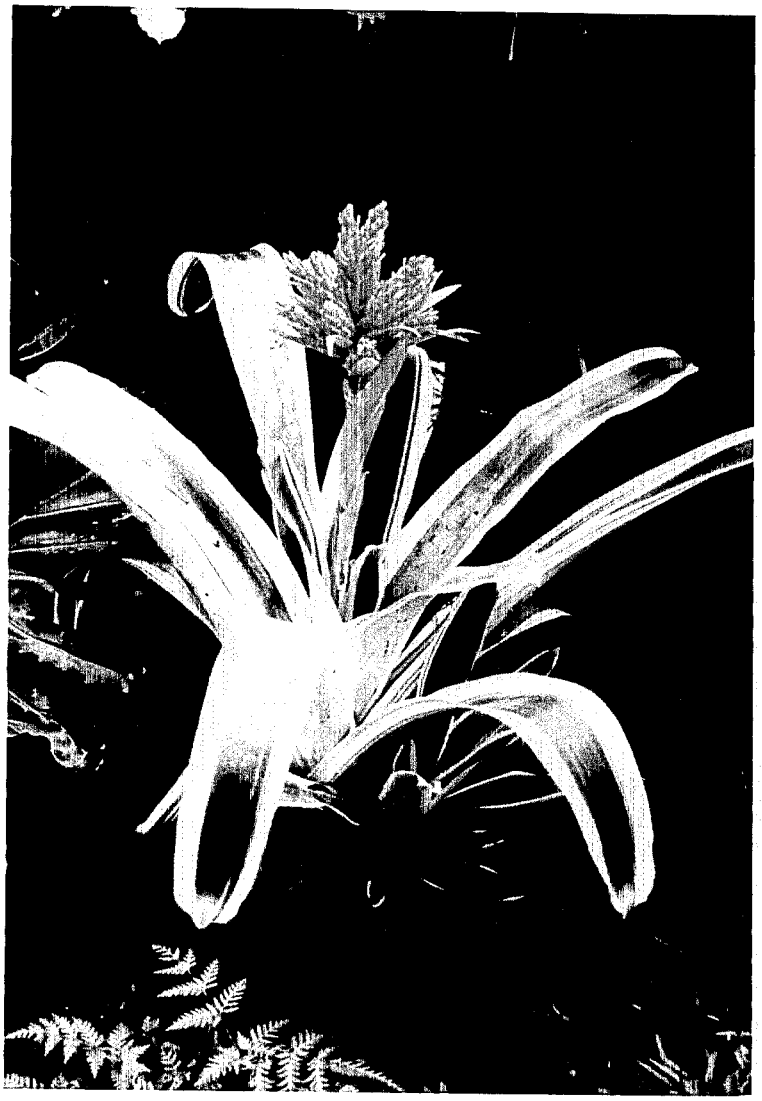
FIG. 1 is a photograph of the *Aechmea fascini* "Variegated Friederike" cultivar of the present invention.
Figure 2:
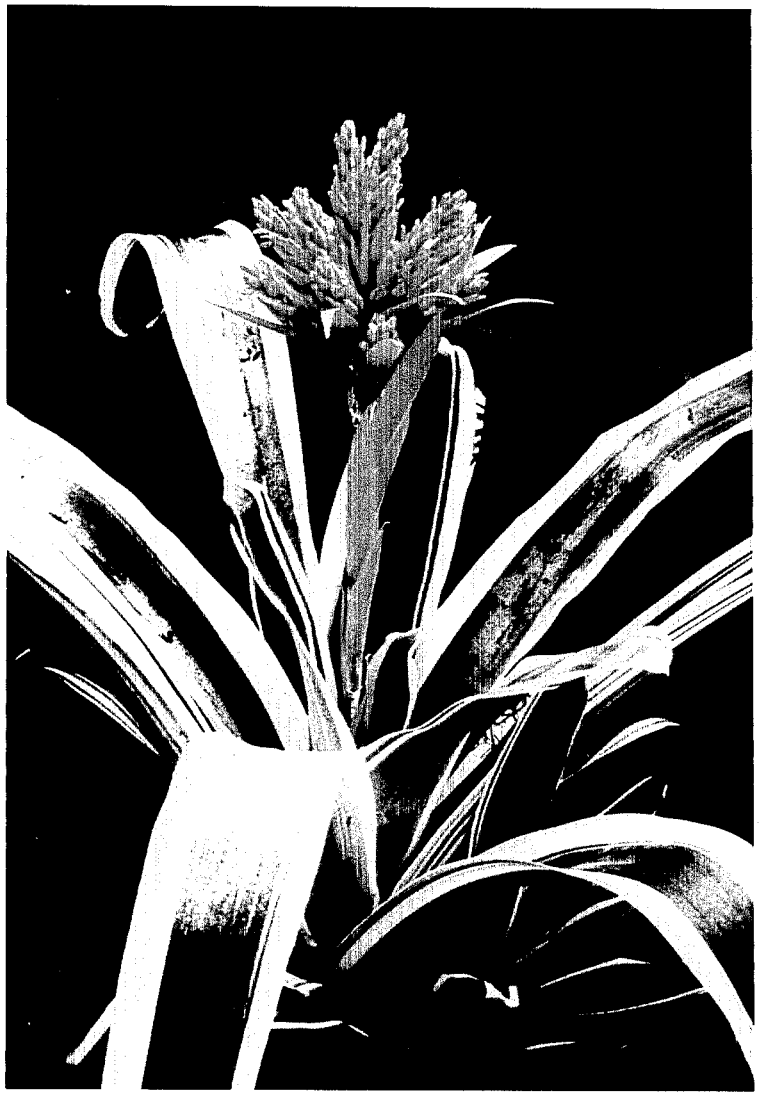
FIG. 2 is a photograph showing the plant in greater detail.
Figure 3:
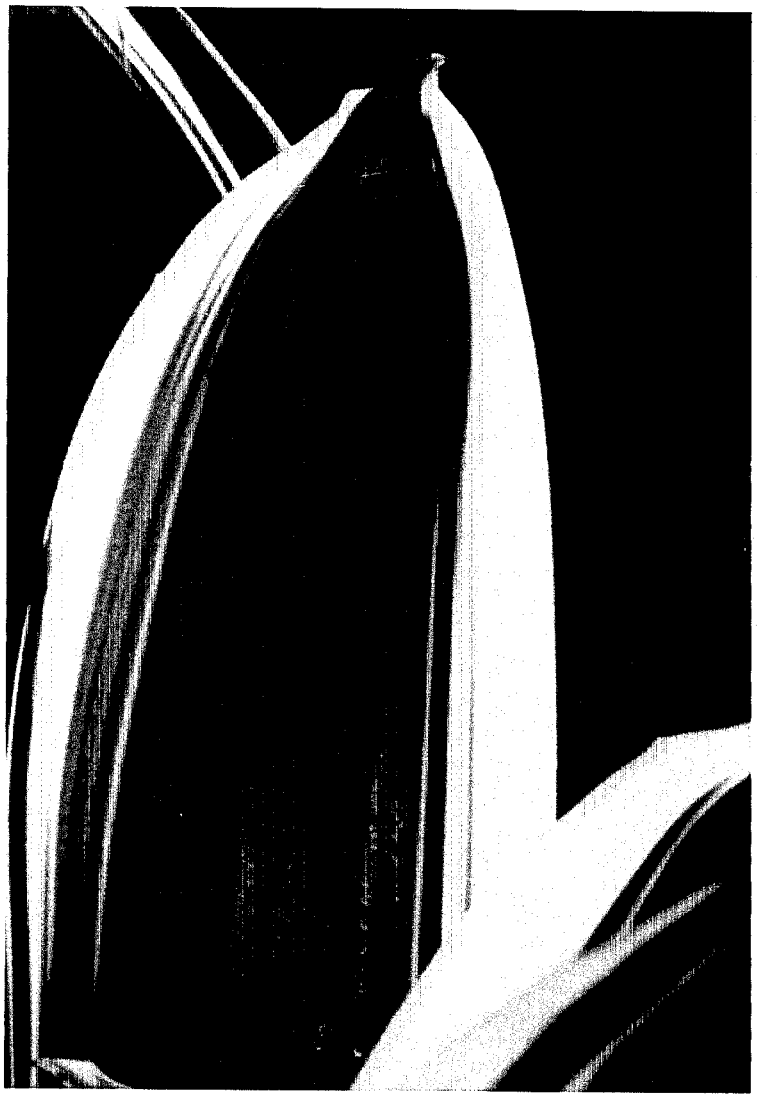
FIG. 3 is a photograph showing the spineless, variegated leaf blade of the new variety.
Figure 4:
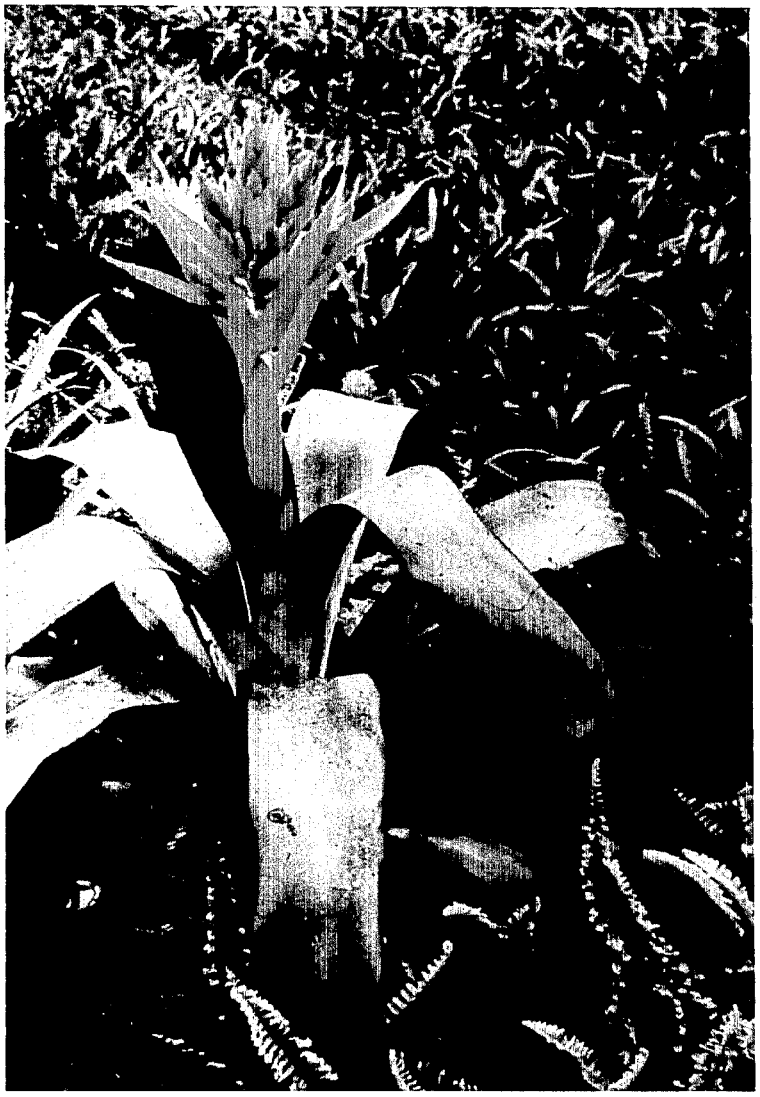
PRIOR ART FIG. 4
FIG. 4 is a photogrpah of a *Aechmea fascini* Friederike showing the substantially uniform color of the leaf blade of that prior art variety.

A further botanical description of the new variety follows. Observed variations that have been noted are that the stripes can vary in breadth and that the color of the leaves may vary as well depending upon environmental influences such as temperature, light intensity, manuring, etc. In intense light, the white stripes can take on a reddish coloration. The reproductive organs of this plant have not been systematically observed.

Color determinations are those determined by the Federal Office for Plant Varieties in Hannover according to the Color Table of the International Code of Nomenclature for Cultivated Plants.

Plant shape: Stemless, reaching 70 to 80 cm in height when blooming.

Foliage: Numerous leaves, forming an upright-spreading funnel-shaped rosette with a height of up to 50 cm and being up to 50 cm in diameter.

Leaf:

*Sheath.*—Indistinctly set off against the scape, having a length of up to 9 cm and a width of up to 8 cm, the upper sides nearly bare, pale green, pale violet in the middle, the margins showing white cream-yellow color separated by thin green stripes, the under sides bein densely covered with white scales.

*Blade.*—Wide and tongue-shaped (ligulated), up to 9 cm wide and up to 35 cm long, contracted in a very short, mostly backward bending tip, having smooth spineless margins showing white cream-yellow color separated by thin green stripes, the upper side initially densely covered with grey scales, the bottom side being covered with silvery white scales.

Scape: Upright, longer than the rosette leaves, about 50 cm long and 1 cm thick, round, reddish green, with dense white woolen hair clinging to the scape.

*Bracts.*—Upright, clinging to the scape, longish-lanciformly pointed, the central bracts being up to 12 cm long and 2 cm wide, both sides scatteredly lepidote, mostly having spines in the margins towards the tip, shiny carmine.

Inflorescence: Loosely bipinnate, 15 cm long, generally 10 cm wide, having generally uprightly spread-out spikes.

Primary bracts: Similar to the upper scape bracts, mostly longer than the spikes.

Spikes: Roundish, having a length of up to 10 cm and a width of up to 2 cm, pointed, having a short, flattened, white-fluffy peduncle with a length of 1 cm.

Flower bracts: The basal ones are arranged in two rows, the central and upper ones being arranged scatteredly, being up to 2.5 cm long (spread out) and 1.5 cm wide, acutely pointed, carinate towards the tip, shiny vermilion at the upper half, greenish towards the base, at the bottom sides white lepidote, surpassing the sepals in height.

Sepals: Up to 1.5 cm long, up to 1 cm wide, almost naked, indistinctly keeled, very short pointed.

Petals: 2 cm in length, upright, blue on the tips, reddish towards the base, no ligula.

Stamens and pistil: Encased.

Ovary: 07 cm high, 5 mm thick.

What is claimed is:

1. A new and distinct variety of *Aechmea fascini* Friederike plant, substantially as herein shown and described and characterized particularly as to novelty by spineless, variegated leaf margins.

* * * * *